United States Patent [19]

Lee et al.

[11] Patent Number: 5,098,294
[45] Date of Patent: Mar. 24, 1992

[54] DENTAL IMPLANT

[76] Inventors: Chong J. Lee, 291-1, Namgajwa-Dong, Seodaemun-Gu, Seoul; Dong S. Kim, 5-5,852-744, Mia 7-Dong, Dobong-Gu, Seoul, both of Rep. of Korea

[21] Appl. No.: 720,393
[22] Filed: Jun. 25, 1991

[30] Foreign Application Priority Data

Feb. 1, 1991 [KR] Rep. of Korea ............... 91-1738

[51] Int. Cl.$^5$ ............................................. A61C 8/00
[52] U.S. Cl. ...................................... 433/169; 433/173
[58] Field of Search ............... 433/169, 173, 174, 175, 433/176

[56] References Cited

U.S. PATENT DOCUMENTS

| | | | |
|---|---|---|---|
| 4,927,363 | 5/1990 | Schneider | 433/169 |
| 4,950,161 | 8/1990 | Richter | 433/169 |
| 5,033,962 | 7/1991 | Scatena | 433/169 |

Primary Examiner—Cary E. O'Connor
Attorney, Agent, or Firm—Ladas & Parry

[57] ABSTRACT

A dental implant comprises an elongated body and a supporting ring each with a concave surfaces which cooperate to secure a shock force dampening member so as to simulate natural tooth movement. The components of the implant are tensioned together in the presence and absence of chewing forces to prevent foreign particle invasion between and into the components of the implant. Optionally, an adhesive bonds the elongated body and the supporting ring to the shock force dampening member further preventing foreign particle invasion between and into the components of the implant. The implant is secured to the jaw bone by a socket or the like.

13 Claims, 2 Drawing Sheets

PRIOR ART

DENTAL IMPLANT

BACKGROUND OF INVENTION

Field of the Invention

The invention relates to a dental implant utilizing a single shock force dampening member to dampen chewing forces, and more particularly, to an implant which greatly reduces the chances of foreign particle invasion between the components which make up the implant.

RELATED APPLICATION

This application is an improvement over the implant disclosed in Korean Patent Application No. 90-10696, filed July 14, 1990, entitled "DENTAL IMPLANT" and the equivalent U.S. patent application Ser. No. 574,486, filed Aug. 28, 1990, now U.S. pat. No. 5,006,068 (hereinafter referred to an "prior application").

Information Disclosure Statement

Dental implant systems are designed to mimic the natural tooth's ability to deal with the forces encountered in chewing in both tooth movement and tooth shock absorbing characteristics.

Although prior art dental implant systems are intended to simulate the action of a natural tooth, the present invention is intended to improve dental hygiene by eliminating the probability of contamination due to the invasion of foreign materials such as bacteria, foot particles or the like, into the implant itself while maintaining a natural toothy like response to the chewing forces received in use. In addition the invasion of foreign material impairs the mechanical operation of the implant itself which further increases the probability of patient discomfort.

Therefore, an object of the present invention is to provide a dental implant which simulates the force dampening effect of a natural tooth.

Another object of the present invention is to provide a dental implant which decreases the probability of foreign particle contamination due to the invasion of foreign material.

A further object of the present invention is to provide a dental implant utilizing a single shock force dampening member to attenuate the forces received by the implant during chewing.

A further object of the present invention is to provide a dental implant which is relatively inexpensive to manufacture.

The preceding objects should be construed as merely presenting a few of the more pertinent features and applications of the invention. Many other beneficial results can be obtained by applying the disclosed invention in a different manner or modifying the invention within the scope of the disclosure. Accordingly, other objects and a fuller understanding of the invention may be had by referring to both the Summary of the Invention and the Detailed Description, below, which describe the preferred embodiment in addition to the scope of the invention defined by the claims considered in conjunction with the accompanying drawings.

SUMMARY OF THE INVENTION

The dental implant of the present invention is defined by the claims with a specific embodiment shown in the attached drawings. For the purpose of summarizing the invention, the invention relates to a dental implant for placement into the jaw bone and comprises an elongated body having an upper end and a lower end, with the lower end of the elongated body terminating in a concave surface and with a bore extending through the elongated body. An artificial tooth securing means, such as a bolt, cement or the like, secures the artificial tooth to the upper end of the elongated body. A shock force dampening member attenuates shock received by the elongated body during use. That is, the dampening member cushions the chewing force and conveys the attenuated chewing force through the rest of the implant toward the jaw bone where the remaining force is absorbed. The dampening member has an aperture formed through it and is configured to be received against the concave surface of the elongated body. A supporting ring supports the shock dampening member and has an upper surface and a lower surface, with the upper surface receiving, in use, the shock force dampening member. An opening extends through the supporting ring. The bore of the elongated body, the aperture of the shock force dampening member and the opening of the supporting ring interconnect with each other to form a passageway. Adhesive means bond the concave surface of the elongated body and the upper surface of the supporting ring, which are in contact with the shock force dampening member, to the shock force dampening member. This seals the surfaces of the elongated body, the shock force dampening member and the supporting ring to protect against the invasion of foreign material between the concave surface of the elongated body and the upper surface of the supporting ring which are in bonded contact with the shock force dampening member. A jaw bone securing means secures the implant in use to the jaw bone. The lower surface of the supporting ring is in contact with the jaw bone. securing means. A passageway securing means, configured to extend in the passageway, secures the elongated body, the shock force dampening member and the supporting ring to the jaw bone securing means and permits, in use, the elongated body to move relative to the jaw bone securing means and the passageway securing means. Such movement enables the shock force dampening member to attenuate chewing forces generated in use against the implant. The passageway securing means also tensions the elongated body, the shock force dampening member and the supporting ring against the jaw bone securing means to ensure protection against foreign material invasion into the implant in the absence of a chewing force.

Preferably, the shock force dampening member is a donut shaped resilient body having a convex surface which matches or fits into the concave surfaces of the elongated body and the supporting ring, respectively. In the preferred embodiment, the upper surface of the supporting ring is concave.

In the preferred embodiment, the bore of the elongated body further includes a first diameter portion and a second diameter portion with the first diameter portion of the bore being greater than the second diameter portion of the bore. Preferably, the passageway securing means comprises a foundation shaft with a first end terminating in a head which has a diameter greater than the second diameter portion of the bore to prevent the first end of the shaft from passing completely through the bore and with a second end being threaded and having a diameter less than the second diameter of the bore to permit the second end of the foundation shaft to pass into the passageway. The jaw bone securing means is preferably a socket secured into the jaw bone with a threaded cavity for receiving the threaded second end of the foundation shaft to threadably secure and tension the elongated body, the shock force dampening member and the supporting ring such that upon the artificial tooth receiving a chewing force, the artificial tooth and the elongated body move vertically downward relative to the head of the foundation shaft to convey the force to the shock force dampening member, the supporting ring and to the socket. In the absence of a chewing force being received by the implant, the foundation shaft maintains tension on the elongated body, the shock force dampening member and the supporting ring against the jaw bone securing means to ensure protection against foreign particle invasion between the components of the implant.

The first diameter portion of the bore of the elongated body preferably includes threads. The artificial tooth securing means is a bolt with external threads to threadably engage the threads of the elongated body to secure the artificial tooth to the elongated body.

The vertical chewing forces are dampened by the shock force dampening member, and the lateral forces associated with chewing are dampened by the degree of the fit of the foundation shaft into the passageway, especially the bore of the elongated body and the opening of the supporting ring.

The more pertinent and important features of the present invention have been outlined above in order that the detailed description of the invention which follows will be better understood and that the present contribution to the art can be fully appreciated. Additional features of the invention described hereinafter form the subject of the claims of the invention. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

BRIEF DESCRIPTION OF THE DRAWINGS

For fuller understanding of the nature and objects of the invention, reference should be had to the following detailed description taken in conjunction with the accompanying drawings in which.

Similar reference characters refer to similar parts throughout the several views of the drawings.

DETAILED DESCRIPTION OF THE INVENTION

Figure 1:
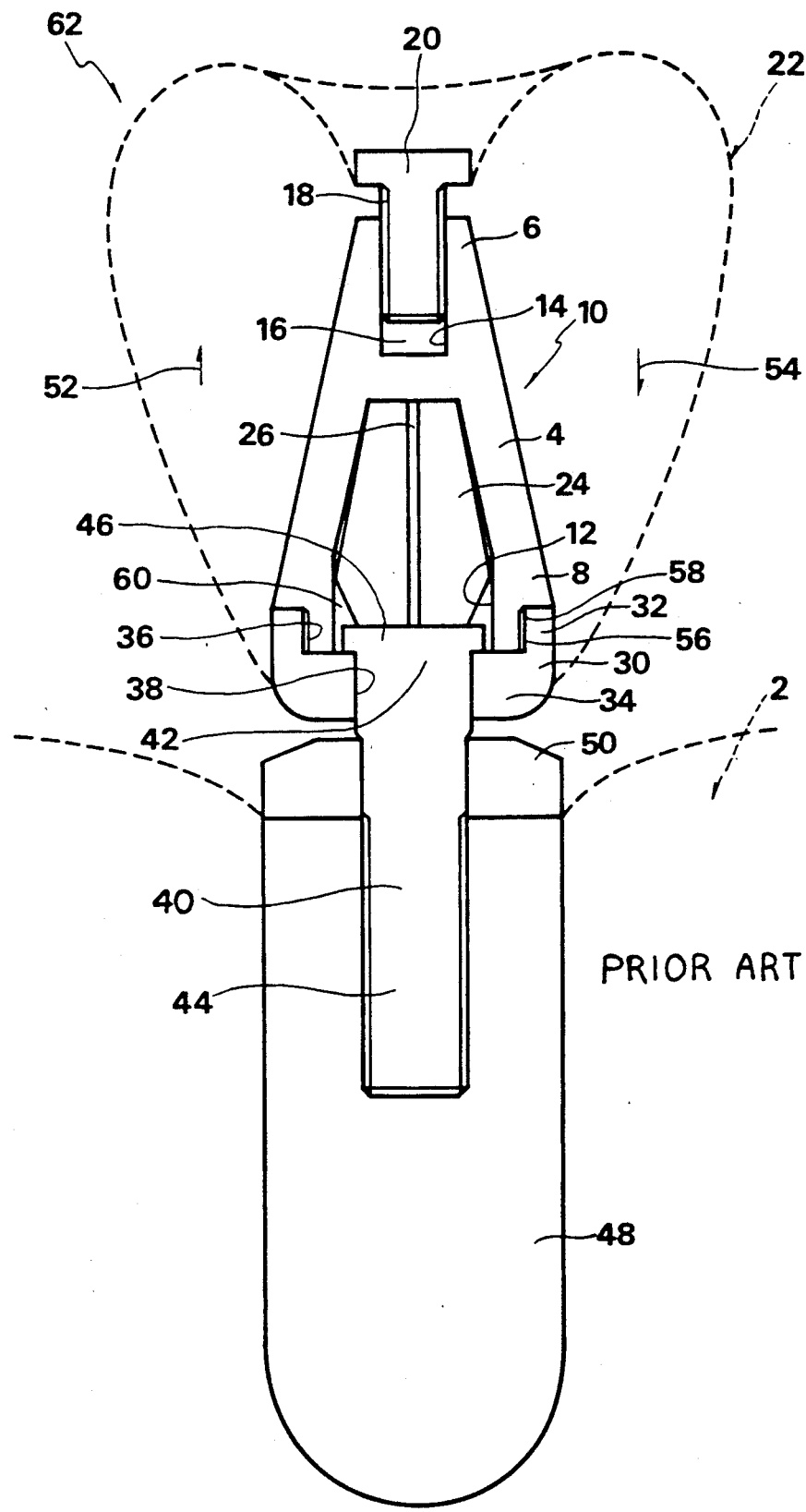
FIG. 1 is a sectional view of the dental implant of the prior application in an assembled condition.

The construction of the implant of the prior application is shown in FIG. 1 which illustrates the dental implant 10 fixed into the jaw bone 2. The elongated body 4 has a first end 6 and a second end 8, with the second end having frustum shaped aperture 12 formed therein.

At the first end 6 of the elongated body 4 a bore 16 is formed having internal threads 14. A bolt 20 having external threads 18 threadably engages the internal threads 14, so that an artificial tooth 22 can be attached at the first end 6 of the elongated body 4.

In the frustum shaped aperture 12 formed in the elongated body 4 is placed a bi-frustum shaped shock force dampening means 24 of resilient rubber silicon. The dampening means 24 substantially fills the frustum shaped aperture 12. An opening 26 is formed at the center of the dampening means 24 and extends therethrough.

A carrier body 30 with a first end 32 and a second end 34 is utilized. The carrier body 30 includes a first aperture 36 and a second aperture 38, with the second aperture 38 having a smaller diameter than that of the first aperture 36.

A foundation shaft 40 with a first end 42 and a second end 44 is employed. The first end 42 of the foundation shaft 40 terminates in a head 46. The diameter of the head 46 is smaller than that of the first aperture 36 of the carrier body 30 and larger than that of the second aperture 38 of the carrier body 30. The diameter of the first end 42 of the foundation shaft 40 is slightly smaller than that of the second aperture 38 of the carrier body to permit the passage of the second end 44 of the foundation shaft 40 therethrough. The second end 44 of the foundation shaft 40 terminates in a jaw bone securing means 48 which fixes the dental implant to the jaw bone 2.

A support ring 50 is secured, utilizing a press fit for example, proximate the first end 42 of the foundation shaft and is spaced apart relative to the second end 34 of the carrier body 30. This structural arrangement limits axial movement of the carrier body in the direction 52 toward the crown by the head 46, and also limits axial movement of the carrier body in the direction 54 toward the jaw bone beyond the supporting ring 50.

To secure the second end 8 of the elongated body 4 to the first end 32 of the carrier body 30, the first aperture 36 formed in the carrier body includes internal threads 56 and the second end 8 of the elongated body 4 includes external threads 58. This enables the external threads 58 of the elongated body 4 to be threadably engaged by the internal threads 56 of the carrier body 30 to secure the elongated body 4 including the artificial tooth 22 to the carrier body 30.

The vertical chewing forces are dampened by the shock force dampening means 24, and the lateral forces associated with chewing are dampened by the degree of the fit of the foundation shaft 40 into the second aperture 38 of the carrier body.

In use, the opening 26 together with the peripheral void 60 between the frustum jaw bone securing means 48, the displacement of the piston operated tooth assembly 62 with respect to the shock force dampening means 24 is along its axis of symmetry thereby mirroring natural tooth movement.

Figure 2:
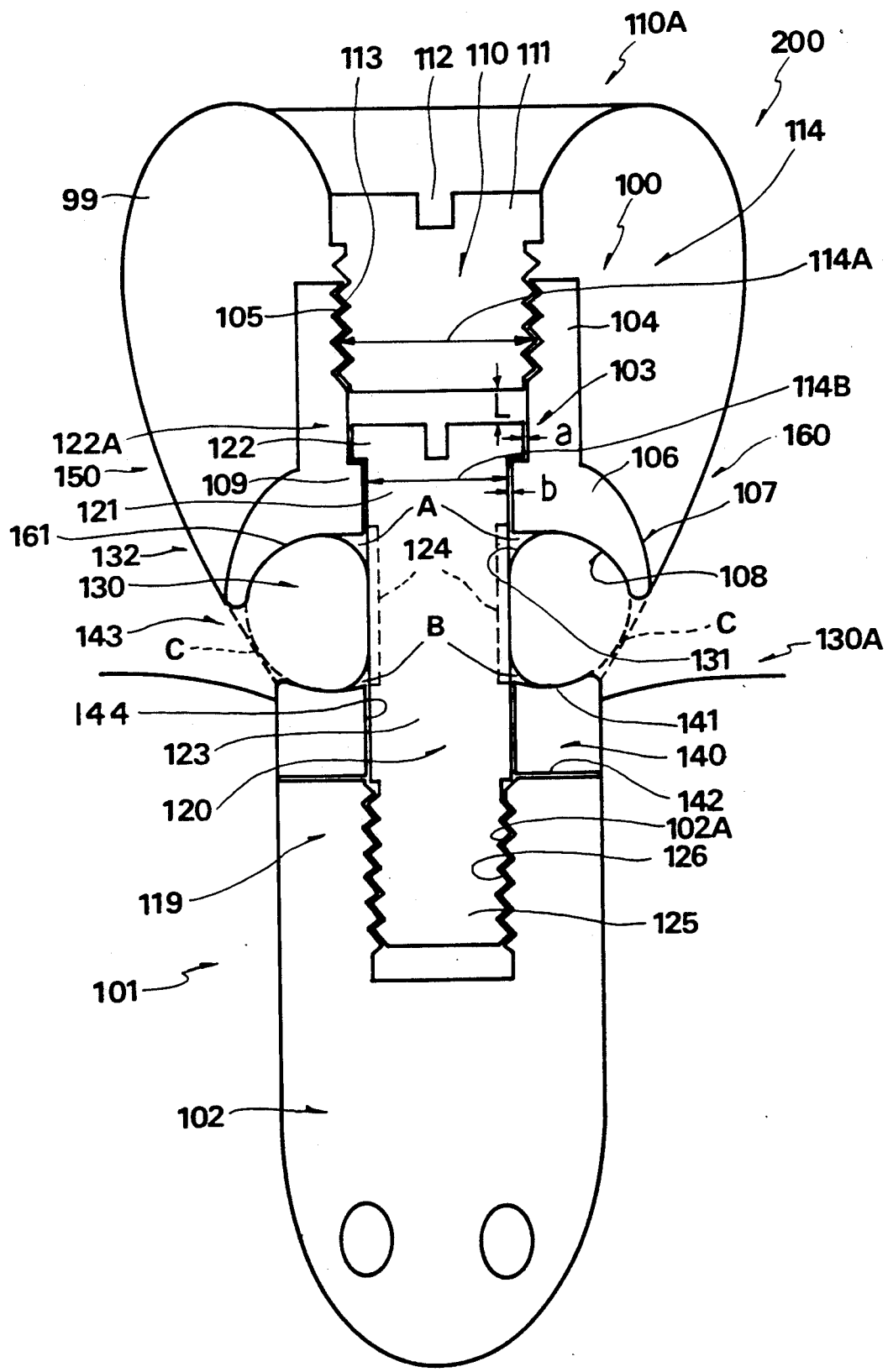
FIG. 2 is a sectional view of the dental implant of the present invention in an assembled condition.

FIG. 2 illustrates the dental implant 200 of the present invention fixed into the jaw bone 101.

The elongated body 103 consists of an upper part 104 and a lower part 106 with a bore 114 extending therethrough. The inner surface of the bore in the upper part 104 of the body 103 includes internal threads 105. The lower part 106 of the elongated body terminates in a concave surface 108.

More specifically, the exterior surface of the lower part 106 of the elongated body defines a convex surface 107; whereas, the interior surface of the lower part 106 defines a concave surface 108. However, the convex shape 107 of the exterior surface of the lower part 106 is not critical.

The bore 114 of the elongated body preferably includes a first diameter portion 114A and a second diameter portion 114B with the first diameter portion being greater than the second diameter portion. Where the diameter portions 114A, 114B of the bore meet, a shoulder 109 is defined. The head of the foundation shaft abuts against the shoulder 109 to limit upward movement of the elongated body, shock force dampening member and supporting ring.

The passageway securing means 119 preferably includes the foundation shaft 120 with a first end 121 terminating in a head 122 having a diameter 122A greater than the second diameter portion 114B of the bore 114 to prevent the head 122 of the foundation shaft 120 from passing completely through the bore. The second end 125 of the foundation shaft 120 is threaded. The second end 125 and the main body 123 of the foundation shaft have a diameter less than the second diameter portion 114B of the bore to permit entrance of these into the passageway. The girth of the foundation shaft 120, including the head, is a little less than the size of the first and second diameter portions of the bore to enable the elongated body to slide along a portion of the main body 123 of the foundation shaft 120, as illustrated as "a" and "b" in FIG. 2. Also, the dimensions of the clearances "a", "b" can be determined to allow lateral movement of the artificial tooth 99 and the elongated body 103 against the chewing force to further simulate natural tooth movement.

An alternative passageway securing means comprises the head of the foundation shaft abutting against the upper part of the elongated body such that the elongated body is placed entirely below the head of the foundation shaft. In this arrangement the artificial tooth 99 is secured to the external surface of the elongated body. An orifice is formed in the bottom of the tooth in order that the tooth is spaced apart from the head of the foundation shaft to allow downward movement of the artificial tooth, elongated body and the dampening member (compression), i.e., intrusion of the head into the orifice.

The jaw bone securing means 101 is a socket 102, or the like, secured into the jaw bone. The socket 102 has a threaded cavity 102A formed therein for receiving the threaded 126 second end 125 of the foundation shaft 120. Thus, the foundation shaft 120 can be threadably secured into the socket to tension the elongated body, the shock force dampening member and the supporting ring such that when the artificial tooth receives a chewing force, the artificial tooth and the elongated body move vertically downward, relative to the head 122 of the foundation shaft 120, to convey the force to the shock force dampening member 130 and to the socket. In the absence of a chewing force being received by the implant, the passageway securing means 119, such as the foundation shaft 120, tensions the elongated body, the shock force dampening member and the supporting ring against the jaw bone securing means to ensure protection against foreign particle invasion between the components of the implant so tensioned.

The artificial tooth securing means 110A secures an artificial tooth 99 to the upper part 104 of elongated body 103. The artificial tooth securing means includes a bolt 110 having external threads 113 which can be screwed into the internal threads 105 formed on the internal surface of the upper part 104 of the elongated body 103 to secure the artificial tooth 99 to the elongated body 103. A slot 112 for a bladed driver is formed at the head 111 of the bolt 110 so that the tooth may be easily adjusted or replaced. However, other such artificial tooth securing means include other mechanical fasteners and curable polymeric cements or glues.

The shock force dampening member 130 attenuates the shock received by the elongated body during chewing and is configured to be received against the concave surface 108 of the elongated body. That is, the shock force dampening member acts like a spring which dissipates the chewing force upon its compression by such force. Preferably, the shock force dampening member 130 is a donut shaped resilient body 130A having a convex surface 132 which matches the contour of the concave surfaces 108, 143 of the elongated body 103 and the supporting ring 140, respectively. The donut 130A further includes an aperture 131 formed therethrough. the concave surfaces of the elongated body and the supporting ring cooperate to keep the donut 103A positioned against the foundation shaft by directing the chewing force inward toward the foundation shaft thereby pushing the donut inward and by providing a physical barrier. The ends of the concave surfaces 108, 143 are spaced apart in use from one another to enable the dampening member to deform outwardly into this space upon compression due to the action of the chewing force. Absent such dampening member structure, the dampening member tends to move about or distort outwardly which increases the chances for foreign particles to lodge in or between the components of the implant during use. Invasion is especially prone to occur between the distorted dampening member and the implant components in immediate contact with it. Distortion outwardly of the dampening member means that the components of the implant are not tensioned equally against each other which increases the chances for particle invasion between the components of the implant.

The supporting ring 140 supports the shock dampening member 130 and has an upper surface 141 and a lower surface 142. The upper surface 141 is in contact with the surface of the shock force dampening member. An opening is formed in the supporting ring and extends through the ring. The bore 114 of the elongated body, the aperture 131 of the shock dampening member and the opening 144 of the supporting ring together form a passageway 150. Preferably, the upper surface 141 of the supporting ring is concave 143 and matches the contour of the convex surface 132 of the shock dampening member where it contacts the supporting ring.

The adhesive means 160 bonds together the concave surface of the elongated body and the upper surface of the supporting ring which are in contact with the shock force dampening member to protect against the invasion of foreign material between the concave surface of the elongated body and the upper surface of the supporting ring in contact with the shock force dampening member. The adhesive means includes adhesives 161, represented as thickened lines in FIG. 2, which cure to an elastic adhesion. Such adhesives are known in the art, such as epoxy resin.

The jaw bone securing means secures the implant to the jaw bone. Such means are well known in the art, for example a socket 102 (Interpore IMZ) manufactured by Interpore International.

The passageway securing means 119 extends in the passageway and secures the elongated body, the shock force dampening member and the supporting ring to the jaw bone securing means. The passageway securing means permit in use the elongated body to move relative to the jaw bone securing means and the passageway securing means. That is, the elongated body 103 is slidably positioned on the passageway securing means. the passageway securing means enable the shock force dampening member to attenuate chewing forces generated against the implant and transmitted to the shock force dampening member. Moreover, the passageway securing means tensions the elongated body, the shock force dampening member and the supporting ring against the jaw bone securing means to ensure protection against foreign material invasion into the implant in the absence of a chewing force. Thus, both the tensioning by the passageway securing means and the adhesive means act to prevent the invasion of foreign material, such as food particles and the like, into and between the elements which comprise the implant.

Optionally, opposite the shock dampening member 130, a notch 124 can be formed on the surface of the main body 123 of the foundation shaft 120 to receive the donut 130A when it is deformed during use, i.e. when the implant is tensioned by the chewing forces. Also, deformation spaces. "A" and "B" can be provided when constructing the donut shaped 130A dampening member 130. These spaces provide room for the donut to occupy during the application of chewing forces.

The donut 130A is preferably composed of silicon rubber of a similar resilient composition. However, the composition of the shock force dampening member should be oil resistant, physiologically inert, stable at high and low temperatures and flexible at low temperature. The shape can be easily obtained by molding.

The lower surface 142 of the supporting ring 140 is a horizontal surface to correspond to the upper surface of the jaw bone securing means 101.

A description of the process of assembly of the dental implant of the present invention follows.

First of all, the foundation shaft 120 is inserted into the bore of the elongated body 103. The head 122 of the foundation shaft 120 contacts the shoulder 109 of the elongated body 103 thereby obstructing further passage. The concave surfaces of the elongated body and the supporting ring and at least part of the convex surface of the shock force dampening member are coated with an adhesive. The foundation shaft 120 then is passed through the aperture of the shock force dampening member 130 and through the opening of the supporting ring 140 and into the threaded cavity of the socket. The foundation shaft 120 is then screwed into the socket by utilizing a bladed driver, or the like, in the slot 122A on the head 122 of the foundation shaft 120. The degree of tension on the shock force dampening member 130 can be adjusted by the number of turns of the foundation shaft. The shock force dampening member is constructed and positioned between the elongated body and the supporting ring which are tensioned together by turning the foundation shaft such that under a no-load condition the dampening member either almost protrudes or just slightly protrudes from a line "C" interconnecting the elongated body and the supporting ring as illustrated at FIG. 2. This side in preventing the invasion of particles of food during chewing into and between the components of the implant.

After the assembling the implant as described above, the bolt 110, via the external threads 113, is screwed into the internal threads 105 of the upper part 104 of the elongated body 103 to attach the artificial tooth assembly 100 to the of the implant.

In consideration of the degree of the maximum compressed displacement of the shock force dampening member 130, the spacing "L" between the upper and surface of the head 122 of the foundation shaft 120 and the lower surface of the bolt 110 can be determined in advance. The precise size of the foundation shaft 120 and the supporting ring 140 is determined in accordance with the size of the existing natural teeth of the patient to whom the dental implant is to be applied to match the natural teeth. This provides an advantage in that the height of the tooth can be easily attained by merely providing different sized shock force dampening members.

It is appreciated by those skilled in the art that there is difference in the chewing force exerted depending on the patient. Thus, it is preferable that the shock force dampening member 130 be designed to meet the requirements of the natural tooth of a patient by adjusting the material and the size of the dampening member 130.

The present invention as described above has the effect that it can meet the requirements of the natural tooth and also prevent the invasion of foreign materials by the sealed condition of each component due to the tensioning of the components and the use of an adhesive on the shock force dampening member, as described above.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A dental implant for placement into a jaw bone, said dental implant comprising:
    an elongated body (103) having an upper part (104) and a lower part (106), with said lower part terminating in a concave surface and with a bore extending through said elongated body;
    an artificial tooth securing means for securing an artificial tooth to said upper part of said elongated body;
    a shock force dampening member (130) for attenuating shock received by said elongated body in use and configured to be received against said concave surface of said elongated body;
    a supporting ring (140) for supporting said shock dampening member (130) and having an upper surface and a lower surface, with said upper surface receiving, in use, said shock force dampening member and having an opening extending therethrough;
    said shock force dampening member further including an aperture formed therethrough whereby said bore, said aperture and said opening together form a passageway;
    jaw bone securing means for securing said implant in use to the jaw bone; and
    a passageway securing means for securing said elongated body, said shock force dampening member and said supporting ring to said jaw bone securing means to permit in use said elongated body to move relative to said jaw bone securing means and said passageway securing means thereby enabling said shock force dampening member to attenuate chewing forces generated in use against said implant and to tension said elongated body, said shock force dampening member and said supporting ring against said jaw bone securing means to ensure protection against foreign material invasion into said implant in the absence of a chewing force.

2. The dental implant of claim 1 wherein said implant further includes an adhesive means for securely bonding said concave surface of said elongated body and said upper surface of said supporting ring in contact with said shock force dampening member thereby bonding said surfaces together to protect against invasion of foreign material between said concave surface of said elongated body and said upper surface of said supporting ring in contact with said shock force dampening member.

3. The dental implant of claim 1 wherein said shock force dampening member (130) is a donut shaped resilient body having a convex surface.

4. The dental implant of claim 3 wherein said upper surface of said supporting ring is concave.

5. The dental implant of claim 1 wherein said bore of said elongated body further includes a first diameter portion and a second diameter portion with said first diameter portion being greater than said second diameter portion;

said passageway securing means comprises a foundation shaft (120) with a first end terminating in a head having a diameter greater than said second diameter portion of said bore to prevent said head of said foundation shaft (120) from passing completely through said bore and with a second end being threaded and having a diameter less than said second diameter portion of said bore to permit said second end of said foundation shaft to pass into said passageway; and said jaw bone securing means is a socket secured in use into a jaw bone and having a threaded cavity for receiving said threaded second end of said foundation shaft to threadably secure and tension said elongated body, said shock force dampening member and said supporting ring such that upon said artificial tooth receiving a chewing force, said artificial tooth and said elongated body move vertically downward relative to said head of said foundation shaft to convey said force to said shock force dampening member and to said socket and in the absence of a chewing force tensioning said elongated body, said shock force dampening member and said supporting ring against said jaw bone securing means to ensure protection against foreign particle invasion into said implant.

6. The dental implant of claim 5 wherein said first diameter portion of said bore of said elongated body includes threads; and said artificial tooth securing means is a bolt having external threads to threadably engage said threads of said elongated body.

7. A dental implant for placement into a jaw bone, said dental implant comprising:

an elongated body (103) having an upper part (104) and a lower part (106) with said lower part terminating in a concave surface and with a bore extending through said elongated body;

an artificial tooth securing means for securing an artificial tooth to said upper part of said elongated body;

a shock force dampening member (130) for attenuating shock received by said elongated body in use and with said dampening member configured to be received against said concave surface of said elongated body and having an aperture formed therethrough; a supporting ring (140) for supporting said shock dampening member (130) and having an upper surface and a lower surface, with said upper surface receiving, in us, said shock force dampening member and having an opening extending therethrough whereby said bore, said aperture and said opening together form a passageway;

adhesive means for securing said concave surface of said elongated body and said upper surface of said supporting ring in contact with said shock force dampening member thereby by sealing said surfaces to form a bonded unit to protect against invasion of foreign material between said concave surface of said elongated body and said upper surface of said supporting rig in contact with said shock force dampening member;

jaw bone securing means for securing said implant in use to the jaw bone; and a passageway securing means for securing said elongated body, said shock force dampening member and said supporting ring to said jaw bone securing means to permit in use said elongated body to move relative to said jaw bone securing means and said passageway securing means thereby enabling said shock force dampening member to attenuate chewing forces generated in use against said implant and transmitted to said shock force dampening member and to tension said elongated body, said shock force dampening member and said supporting ring against said jaw bone securing means to ensure protection against foreign material invasion into said implant in the absence of a chewing force.

8. The dental implant of claim 7 wherein said shock force dampening member (130) is a donut shaped resilient body having a convex surface.

9. The dental implant of claim 8 wherein said upper surface of said supporting ring is concave such that said concave surfaces of said elongated body and said supporting ring cooperate to keep said donut positioned against said foundation shaft.

10. The dental implant of claim 7 wherein said bore of said elongated body further includes a first diameter portion and a second diameter portion with said first diameter portion being greater than said second diameter portion;

said passageway securing means comprises a foundation shaft 120 with a first end terminating in a head having a diameter greater than said second diameter portion of said bore to prevent said head of said foundation shaft 120 from passing completely through said bore and with a second end being threaded and having a diameter less than said second diameter portion of said bore to permit said second end of said foundation shaft to pass into said passageway; and said jaw bone securing means in a socket secured in use into a jaw bone and having a threaded cavity for receiving in use said threaded second end of said foundation shaft to threadably secure and tension said elongated body, said shock force dampening member and said supporting ring such that upon said artificial tooth receiving a chewing force, said artificial tooth and said elongated body move vertically downward relative to said head of said foundation shaft to convey said force to said shock force dampening member and to said socket and in the absence of a chewing force tensioning said elongated body, said shock force dampening member and said supporting ring against said jaw bone securing means to ensure protection against foreign particle invasion into said implant.

11. The dental implant of claim 10 wherein said first diameter portion of said bore of said elongated body includes threads; and said artificial tooth securing means is a bolt having external threads to threadably engage said threads of said elongated body.

12. A dental implant for placement into a jaw bone, the dental implant comprising:

an elongated body (103) having an upper part (104) and a lower part (106), with said lower part of said elongated body terminating in a concave surface and with a bore extending through said elongated body wherein said bore further includes a first diameter portion and a second diameter portion with said first diameter portion being greater than said second diameter portion;

an artificial tooth securing means for securing an artificial tooth to said upper part of said elongated body;

a shock force dampening member for attenuating shock received by said elongated body in use and with said dampening member configured to be received against said concave surface of said elongated body and wherein said shock force dampening member is a donut shaped resilient body having a convex surface and an aperture formed therethrough;

a supporting ring (140) for supporting said shock dampening member (130) and having an upper surface and a lower surface, with said upper surface receiving, in use, said shock force dampening member and wherein said upper surface of said supporting ring is concave such that said concave surfaces of said elongated body and said supporting rig cooperate to keep said donut positioned against said foundation shaft by directing the chewing force inward toward said foundation shaft;

said supporting ring further including an opening extending therethrough whereby said bore, said aperture and said opening together form a passageway;

adhesive means for securing said concave surface of said elongated body and said upper surface of said supporting ring in contact with said shock force dampening member thereby by sealing said surfaces to form a bonded unit to protect against invasion of foreign material between said concave surface of said elongated body and said upper surface of said supporting ring in contact with said shock force dampening member;

jaw bone securing means for securing said implant in use to the jaw bone;

a foundation shaft (120) with a first end terminating in a head having a diameter greater than said second diameter portion of said bore to prevent said head of said foundation shaft 120 from passing completely through said bore and to permit in use said elongated body to move relative to said jaw bone securing means and said passageway securing means and with a second end being threaded and having a diameter less than said second diameter portion of said bore to permit said second end of said foundation shaft to pass into said passageway; and said jaw bone securing means is a socket secured in use into a jaw bone and having a threaded cavity for receiving in use said threaded second end of said foundation shaft to threadably secure and tension said elongated body, said shock force dampening member and said supporting ring such that upon said artificial tooth receiving a chewing force, said artificial tooth and said elongated body move vertically downward relative to said head of said foundation shaft to convey said force to said shock force dampening member and to said socket and in the absence of a chewing force tensioning said elongated body, said shock force dampening member and said supporting ring against said jaw bone securing means to secure protection against foreign particle invasion into said implant.

13. The dental implant of claim 12 wherein said first diameter portion of said bore of said elongated body includes threads; and said artificial tooth securing means is a bolt having external threads to threadably engage said threads of said elongated body.

* * * * *